(12) United States Patent
Lampronti et al.

(10) Patent No.: US 11,077,116 B2
(45) Date of Patent: Aug. 3, 2021

(54) ISOXAZOLE DERIVATIVES AS INDUCERS OF FETAL HEMOGLOBIN IN ERYTHROID PRECURSOR CELLS FROM BETA-THALASSEMIC PATIENTS

(71) Applicant: RARE PARTNERS SRL, Milan (IT)

(72) Inventors: Ilaria Lampronti, Milan (IT); Roberto Gambari, Milan (IT); Daniele Simoni, Milan (IT)

(73) Assignee: RARE PARTNERS SRL, Milan (IT)

( * ) Notice: Subject to any disclaimer, the term of this patent is extended or adjusted under 35 U.S.C. 154(b) by 18 days.

(21) Appl. No.: 16/631,295

(22) PCT Filed: Jul. 13, 2018

(86) PCT No.: PCT/EP2018/069158
§ 371 (c)(1),
(2) Date: Jan. 15, 2020

(87) PCT Pub. No.: WO2019/016103
PCT Pub. Date: Jan. 24, 2019

(65) Prior Publication Data
US 2020/0206234 A1  Jul. 2, 2020

(30) Foreign Application Priority Data
Jul. 18, 2017 (IT) .................. 102017000081419

(51) Int. Cl.
A61K 31/5377 (2006.01)
A61K 31/42 (2006.01)
A61P 7/06 (2006.01)

(52) U.S. Cl.
CPC .......... *A61K 31/5377* (2013.01); *A61K 31/42* (2013.01); *A61P 7/06* (2018.01)

(58) Field of Classification Search
CPC ....... A61K 31/5377; A61K 31/42; A61P 7/06; C07D 413/12
See application file for complete search history.

(56) References Cited

U.S. PATENT DOCUMENTS 8,383,616 B2 * 2/2013 Giannini ................ A61P 21/00
514/210.2
2016/0113936 A1 4/2016 Brittain et al.

FOREIGN PATENT DOCUMENTS

WO  2010000748 A1  1/2010

OTHER PUBLICATIONS

Anea C. et al., "Cytoprotective chaperone proteins are novel anti-inflammatory targets in Sickle Cell Disease", The FASEB Journal, Apr. 1, 2017, Published on line, pp. 1-3.
Natarajan K, et al., "Heat Schock Protein Inhibition in Sickle Cell Disease: A Novel Approach to Attenuating the Inflammatory Response?" Blood, vol. 110, No. 11, Nov. 16, 2007, p. 2263.
Search Report and Written Opinion of PCT/EP2018/069158 dated Oct. 23, 2018.
Vesci L, et al., "Preclinical antitumor activity of SST0116CL1: A novel heat schock protein 90 inhibitor", International Journal of Oncology, vol. 45, No. 4, Aug. 1, 2014, pp. 1421-1429.

* cited by examiner

*Primary Examiner* — Kamal A Saeed
(74) *Attorney, Agent, or Firm* — Silvia Salvadori, P.C.; Silvia Salvadori

(57) ABSTRACT

The invention refers to the use of isoxazole derivatives to prepare medicament able to induce fetal hemoglobin (HbF) synthesis in β-thalassemia and sickle cell disease (SCD) patients.

5 Claims, 5 Drawing Sheets

ISOXAZOLE DERIVATIVES AS INDUCERS OF FETAL HEMOGLOBIN IN ERYTHROID PRECURSOR CELLS FROM BETA-THALASSEMIC PATIENTS

This application is a U.S. national stage of PCT/EP2018/069158 filed on 13 Jul. 2018, which claims priority to and the benefit of Italian Application No. 102017000081419 filed on 18 Jul. 2017, the contents of which are incorporated herein by reference in their entireties.

FIELD OF THE INVENTION

The present invention refers to the use of isoxazole derivatives to prepare a medicament able to induce fetal hemoglobin (HbF) synthesis in β-thalassemia and sickle cell disease (SCD) patients.

STATE OF THE ART

A therapeutic strategy able to reduce the need for red blood cell transfusions is the induction of HbF using chemical inducers able to stimulate the production of γ-globin chain. It is expected that this potential approach would improve clinical parameters through HbF production and would reduce the excess of α-chain imbalance, decrease the severity of anemia in β-thalassemia patients.

In recent years, much effort has been made to identify new occurring inducers and drug treatments, which can increase the synthesis of HbF and promote the expression of fetal γ-globin genes.

Some chemotherapeutic agents, for example, 5-azacytidine, butyrate and hydroxyurea, (HU) have been characterized, due to their ability to enhance HbF production individually or through various combinations. Yet, most of these currently identified HbF-inducing agents exhibit low efficacy and specificity, myelotoxicity and carcinogenesis as well as modest responses to treatment, which greatly limit their usefulness in the clinical practice. 5-azacitidine was the first drug shown able to increase γ-globin expression. The short-chain fatty acid butyrate was reported to decrease transfusion requirements in transfusion-dependent β-thalassemia patients. It effects are associated to inhibition of histone deacetylation, leading to increase of γ-globin gene expression. Erythropoietin (EPO) has proliferative effects; in fact it is capable of increasing thalassemic erythropoiesis, and exhibits anti-apoptotic properties. Only patients with low endogenous erythropoietin levels have responded to the combination of erythropoietin and butyrate, but without increasing HbF.

At present the only drug approved for γ-globin induction is Hydroxyurea, of which it is still unclear the efficacy. Until today, this drug is used in thalassemia intermedia and sickle-cell disease (SCD) patients. It acts through multiple mechanisms, including cytotoxic activity accelerating the differentiation process and stimulating cellular stress response pathways, leading to an overall increase in the number of F cells.

Most recently, Decitabine and HQK-1001, new fetal globin inducers that stimulate fetal globin induction through the proximal promoter and also exhibit erythropoietic-stimulatory effects, are being studied.

Another potential strategy is to develop techniques to silence HbF suppression as that caused by the BCL11A factor, involved in the γ-globin downregulation. The knockdown of BCL11A expression results in the reactivation of HbF expression.

Subjects affected by severe β-thalassemia and Hereditary Persistence of Fetal Hemoglobin (HPFH) have been considered as a demonstration that increase of the production of HbF and reactivate the γ globin genes might lead to a asymptomatic clinical pattern. As known in several studies, the induction of HbF can reduce the severity of β-thalassemia by improving the imbalance between alpha and β-like globin chains through reduction of free alpha-globin chains. In conclusion, a major goal of the clinical research on these hematological pathologies is focused on the potential therapeutic drugs that could reactivate the γ-globin gene expression in erythroid cells of β-thalassemia and SCD patients.

There are several categories of drugs and most of them are led compounds identified from biological material like plant extracts, fungi and agro-industry material and of possible interest in the field of a pharmacological approach as a therapy of β-thalassemia using molecules able to stimulate the production of HbF in adults.

Among recently identified inducers, representative examples are histone deacetylase inhibitors (Muralidhar S A, et al., J Biol Chem. 2011; 286:2343-53), resveratrol (Bianchi N, et al., Evid Based Complement Alternat Med. 2009; 6:141-51), rapamycin (Mischiati C, et al., Br J Haematol. 2004; 126:612-21) and PNAs (Wang G, Xu X, et al., Nucleic Acids Res. 1999; 27:2806-13).

In this respect, Radicicol is a natural compound, a resorcylic acid lactone, first isolated in 1953 from the fungus *Monosporium bonorden* in a sample of African soil:

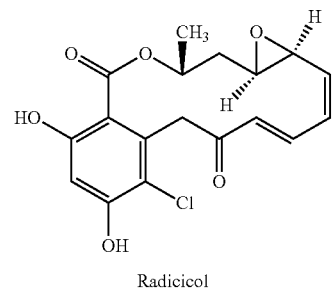 [SMILES: C[C@@H]1C[C@H]2O[C@H]2/C=C\C=C\C(=O)Cc2c(Cl)c(O)cc(O)c2C(=O)O1]

Radicicol

Some years later, the same compound was extracted from the culture filtrate of a strain of *Nectria radicicola* and named 'radicicol'. Thereafter, it was also isolated from several fungi, including *Neocosmospora tenuicristata, Verticillium Chlamydosporium, Pochonia chlamidosporia*, and *Chaetomium chiversii*. The structure of radicicol can competitively disrupt Hsp90 complex formation by binding the N-terminal domain of Hsp90 with great affinity.

HSP90 is a molecular chaperone and one of the most abundant proteins expressed in cells. It is highly conserved and expressed in a variety of different organisms, from bacteria to mammals. In absence of stress condition, HSP90 works as a general protective chaperone, with specific roles, such as assisting in folding, participating in the intracellular transport, maintenance and degradation of proteins as well as facilitating cell signaling. HSP90 participates in many other processes as a key regulator, in oncogenesis leading to self-sufficiency in growth, stabilization of mutant proteins, angiogenesis and metastasis. In fact it is overexpressed in a wide range of human carcinomas.

In contrast to other antitumor compounds, Radicicol has no hepatotoxicity.

Among 4,5-diarilisoxole derivatives, NVP-AUY922, disclosed in US 2016/113936, is in phase II clinical trials:

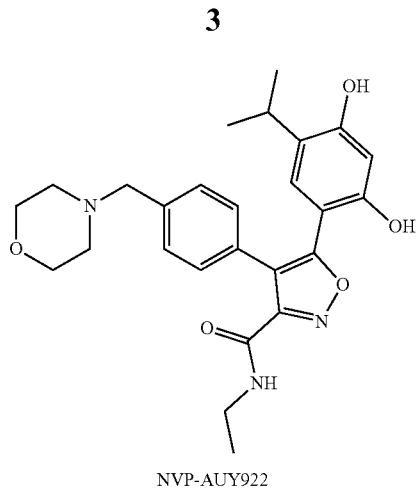

NVP-AUY922

US 2016/113936 does not disclose the induction of Hbf by the disclosed compounds, acting though inhibition of pro-inflammatory and pre-coagulant activities.

DESCRIPTION OF THE INVENTION

Figure 1:
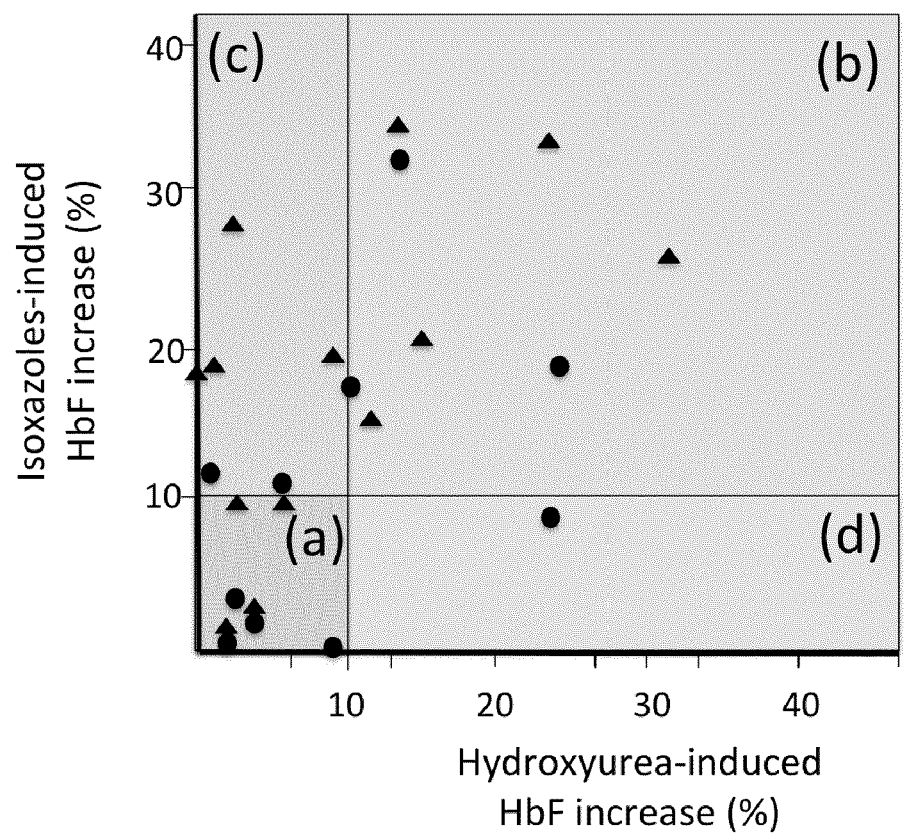
FIG. 1: HbF increase in isoxazoles-treated ErPCs. In (c) the data concer ErPCs showing low levels of HbF induction when treated with HU.

We have now found that isoxazole derivatives characterized by a Resorcinol portion and the C-3 amide moiety show high activity in inducing HbF synthesis in erythroid precursors cells (ErPCs) derived from β-thalassemia patients. These data were verified using ErPCs from an high number of patients with different genotypes and HbF starting levels.

The invention refers in particular to compounds with the following formula I:

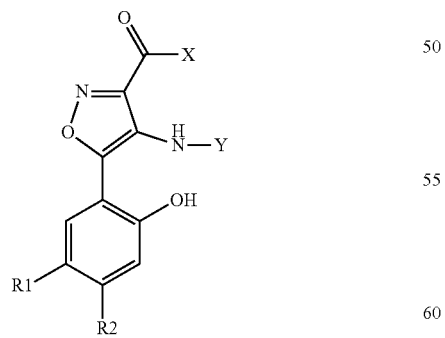

wherein:
R1 is C1-C3 alkyl or chlorine, fluorine, bromine;
R2 is hydroxy or methyl;
X is a C1-C4 alkylamino group or C1-C4 fluoroalkylamino group;

Y is a C2-C4 acyl group, a benzoyl group, optionally substituted with one or more methoxy, heteroaryl moieties, or a group with the following formula:

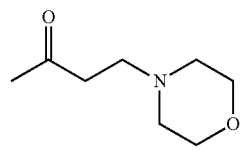

for use as inducers of fetal hemoglobin in the therapeutic treatment of thalassemia and sickle cell disease.

Hetero-aryl moiety means 2- or 3-tiophene-carbonyl, 2- or 3-tiophene-carbonyl, 2- or 3-furan-carbonyl, 3- or 4-oxazolyl carbonyl, 2-, 3- or 4-pyridil carbonyl, optionally substituted with methyl or acetyl groups.

R1 is preferably chlorine or isopropyl.

X is preferably ethylamino or 2,2,2-trifluoroethylamino.

Y is preferably acetyl, tert-butylcarbonyl, para-methoxy benzoyl, 3,4 dimethoxy-benzoyl, 3-methyl-thienyl, 5-acetyl-isoxazolyl.

The compounds of formula I, their synthesis and their activities in inhibiting Hsp90 were disclosed in EP 2 310 377.

Particularly preferred derivatives for use in this invention have structures 1-8 shown

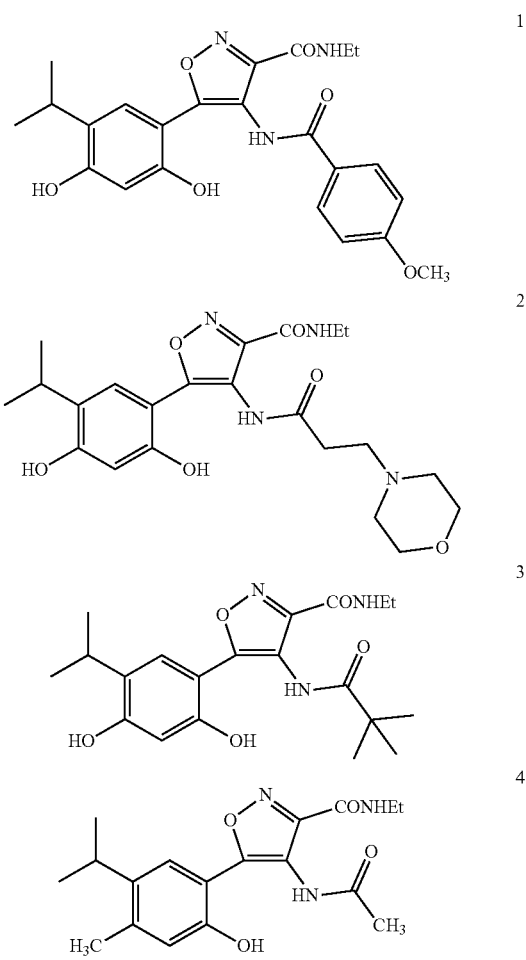

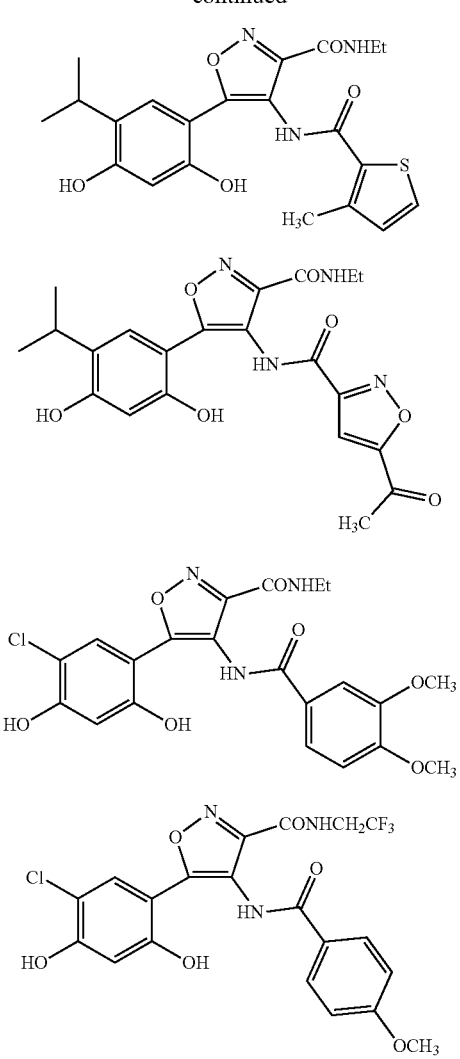

The derivatives 1-8 were shown to be potent HbF inducers in ErPCs from beta-thalassemia patients and may be proposed for the therapy of β-thalassemia. Their activity was even more pronounced than that of the HU. Some isoxazole derivatives are active in inducing HbF also in erythroid precursors that do not respond to HU treatment.

All the derivatives belonging to the general formula I may be utilized in association with other inducers in order to obtain additional or synergic affects.

For instance, the HbF inducing activity of the isoxazole derivatives 1-8 is shown below and it was evaluated through:
- Study on the erythroid differentiation in human erythroleukemic K562 cells;
- Study on the α, ζ, γ, ε globin gene expression in human erythroleukemic K562 cells;
- Study on the γ globin gene expression in erythroid precursor cells from thalassemic patients (RT-qPCR);

Obtained data show that these isoxazole derivatives are potent inducers of erythroid differentiation of K562 cells and they lead to a considerable increase in γ-globin mRNAs in erythroid precursors cells from β-thalassemia patients. The most relevant results for possible applications in experimental therapy for β-thalassemia concern the study of HbF production in erythroid precursors cells form β-thalassemia patients (studied by HPLC) treated with different concentrations of the 1-8 compounds. Examples of the obtained results are showed in the following tables and figures.

Patients were recruited following all the ethical requirements and the approval of the Ethical Committees of Ferrara Hospital. Blood samples were collected from 23 β-thalassemia patients after signature of the informed consent form. The genotype of all these patients was obtained, and summary of the composition of the samples is reported in Table I.

TABLE 1

Genotypes of the patients recruited for the study

| PATIENTS | GENOTYPE |
| --- | --- |
| Th 1 | $\beta^+IVS1\text{-}110/\beta^°39$ |
| Th 2 | $\beta^+IVS1\text{-}6/\beta^°39$ |
| Th 3 | $\beta^+IVS1\text{-}110/\beta^+IVS1\text{-}110$ |
| Th 4 | $\beta^°6(-\Delta)/\beta^+IVS1\text{-}110$ |
| Th 5 | $\beta^°39/\beta^°39$ |
| Th 6 | $\beta^+IVS1\text{-}110/\beta^+IVS1\text{-}110$ |
| Th 7 | $\beta^+IVS1\text{-}110/\beta^°39$ |
| Th 8 | $\beta^+IVS1\text{-}110/\beta^°39$ |
| Th 9 | $\beta^+IVS1\text{-}110/\beta^+IVS1\text{-}110$ |
| Th 10 | $\beta^+IVS1\text{-}110/\beta^°39$ |
| Th 11 | $\beta^°39/\beta^°39$ |
| Th 12 | $\beta^+IVS1\text{-}110/\beta^+IVS1\text{-}110$ |
| Th 13 | $\beta^+IVS1\text{-}110/\beta^°39$ |
| Th 14 | $\beta^+IVS1\text{-}110/\beta^°39$ |
| Th 15 | $\beta^+IVS1\text{-}6/\beta^+IVS1\text{-}6$ |
| Th 16 | $\beta^°39/\beta^°39$ |
| Th 17 | $\beta^+IVS1\text{-}110/\beta^°39$ |
| Th 18 | $\beta^+IVS1\text{-}110/\beta^°39$ |
| Th 19 | $\beta^+IVS1\text{-}6/\beta^°39$ |
| Th 20 | $\beta^+IVS1\text{-}110/\beta^°39$ |
| Th 21 | $\beta^+IVS1\text{-}110/\beta^°39$ |
| Th 22 | $\beta^+IVS1\text{-}1/\beta^°39$ |
| Th 23 | $\beta^+IVS1\text{-}110/\beta^°39$ |

Effect of Selected Isoxazole Derivatives on Cell Growth and Differentiation of the ErPCs (Erythroid Precursor Cells) of β-Thalassemic Patients The effects of isoxazole derivatives on cell growth and differentiation of erythroid precursors cells were determined by employing the two-phase liquid culture system and treated for five days with different concentration of the selected compound.

All the tested isoxazole derivatives demonstrated no cytotoxic effects at the used concentrations determining high level of erythroid differentiation demonstrated by benzidine assay.

Pattern of Hemoglobin Production Detected by HPLC Analysis

HPLC analyses were done on cell lysates derived from ErPCs of 23 patients and, through careful comparative analyses, we have monitored and quantified HbF, adult hemoglobins (HbA$_0$ and HbA$_2$) and the presence of α-aggregates. Generally, excess of α-globin chains is present in thalassemic patients that are deficient in β-globins, causing α-aggregates formation and precipitation. The α-aggregates reduction represents an important clinical result usually detectable in the presence of efficient HbF inducers.

TABLE II

Representative Table of obtained data from HPLC analysis
of hemoglobins expressed in cell cultures derived from
patient Th1 treated with HU, and with compounds 1 and
2. In untreated cells (C−) the HbF starting level is
15.47%, while in the treated cells HbF increased up to
24.51% (HU 100 nM), 30.30% (1, 85 nM) and 21.67 (2, 50 nM).

| Th1 | HbF % | aggregates α % | HbA$_0$ % | HbA$_2$ % |
|---|---|---|---|---|
| C− | 15.47 | 6.70 | 46.54 | 31.29 |
| HU 100 μM | 24.51 | 2.80 | 37.61 | 33.19 |
| #1 85 nM | 30.30 | 5.90 | 42.41 | 21.39 |
| #2 50 nM | 21.67 | 2.81 | 50.70 | 24.82 |

In these erythroid precursor cells both HU and derivatives 1 and 2 are active in inducing HbF.

TABLE III

Representative Table of obtained data from HPLC analysis
of hemoglobins expressed in cell cultures derived from
patient Th10 treated with HU and compounds 1, 2 and 4.
In the untreated precursor cells (C−) the starting level
of HbF is 17.57%, in the cells treated with HU (100 nM)
the reveled level of HbF is similar to the untreated cells
(19.42%), while HbF production increased up to 35.54% (1,
85 nM), 36.36% (2, 50 nM), 30.26-40.80% (4, 85-200 nM).

| Th1 | HbF % | aggregates α % | HbA$_0$ % | HbA$_2$ % |
|---|---|---|---|---|
| C− | 17.57 | 11.15 | 39.26 | 32.02 |
| HU 100 μm | 19.42 | 11.55 | 34.22 | 34.82 |
| #1 85 nM | 35.54 | 2.26 | 36.39 | 25.81 |
| #2 50 nM | 36.36 | 2.02 | 36.34 | 25.29 |
| #4 85 nM | 30.26 | 3.24 | 39.59 | 26.91 |
| #4 120 nM | 34.65 | 2.05 | 38.48 | 24.82 |
| #4 127 nM | 39.19 | 1.28 | 35.73 | 23.80 |
| #4 200 nM | 40.80 | 0.42 | 35.49 | 22.27 |

In these erythroid precursor cells the derivatives 1, 2 and 4 were more active than HU in inducing HbF. The data obtained from HPLC analysis showed in the representative examples reported in Tables II and III, can be summarized as shown in FIG. 1; the data demonstrate that these isoxazoles are very active in inducing HbF synthesis, also in erythroid precursors cells that did not respond to HU treatment.

FIG. 1 (panel c) shows data on the isoxazoles effects on erythroid precursors cells unable to respond to HU treatment in terms of increased HbF production (% HbF increases less than 10%).

Figure 2:
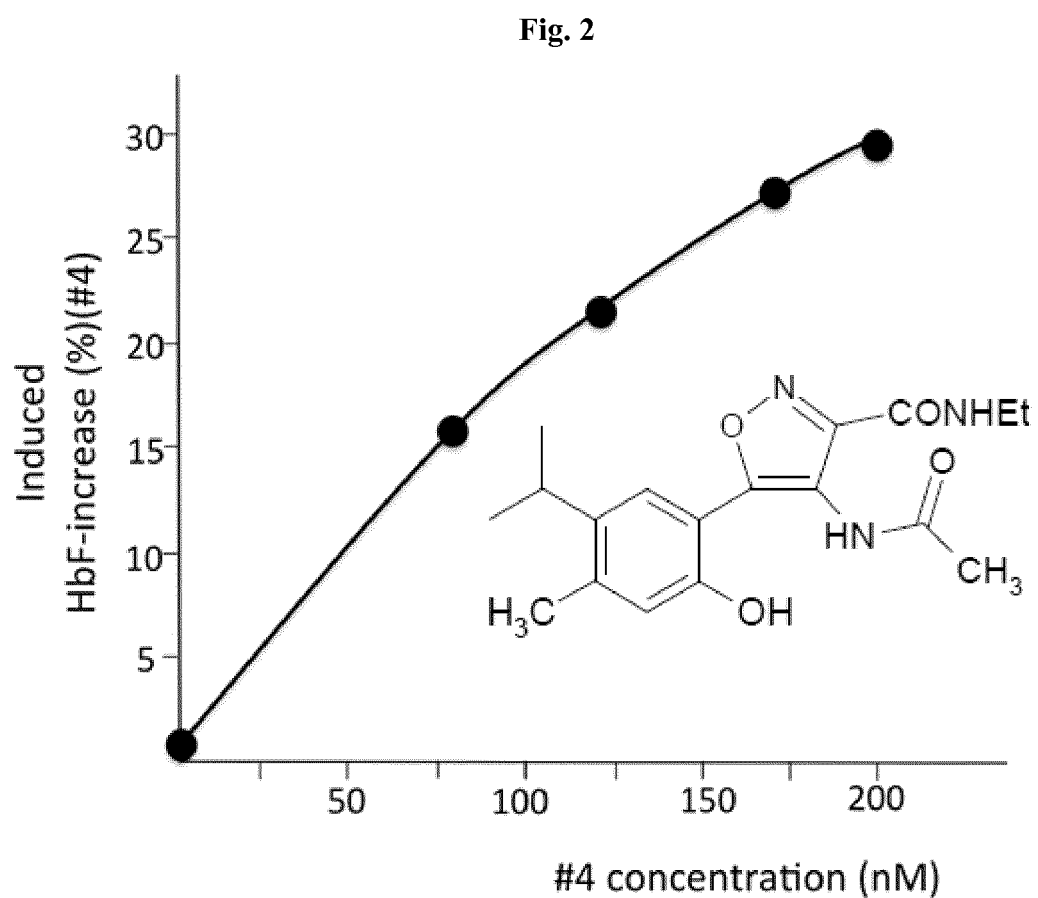
FIG. 2: Concentration-dependent effects of compound 4 in inducing HbF.

FIG. 2 also shows the HbF induction effects, displaying the dose-depending effect of the compound 4 in inducing HbF compared to the increase of induction in erythroid precursors cells.

Alpha-Aggregates Reduction

One the important effects of a good inducer is the ability of decreasing the excess of α-globin chains, leading to presence of α-aggregates with known clinical relevance. The unbalance in the contents of α-globin and β-globin chains is one of the biochemical factors in the physiopathology of β-thalassemia.

Figure 3:
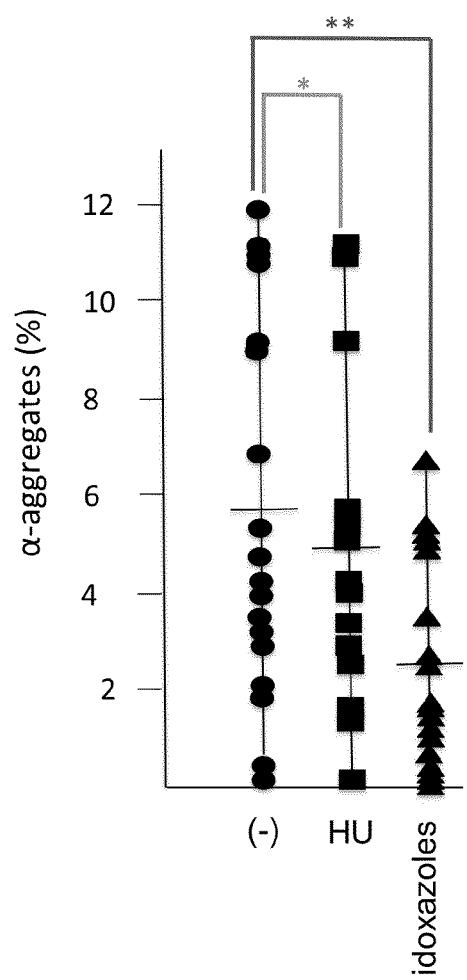
FIG. 3: Decrease of α-aggregates after treatment of ErPCs from β-thalassemia patients with isoxazoles and HU.

FIG. 3 demonstrates that the isoxazoles are most active than HU in reducing α-aggregates levels after treatment of ErPCs derived from β-thalassemic patients in culture for seven days with HU or isoxazoles. FIG. 3 shows the decrease of α-aggregates after treatment of ErPCs from β-thalassemia patients with isoxazoles and HU.

Personalized Response of ErPCs to Isoxazoles

Figure 4:
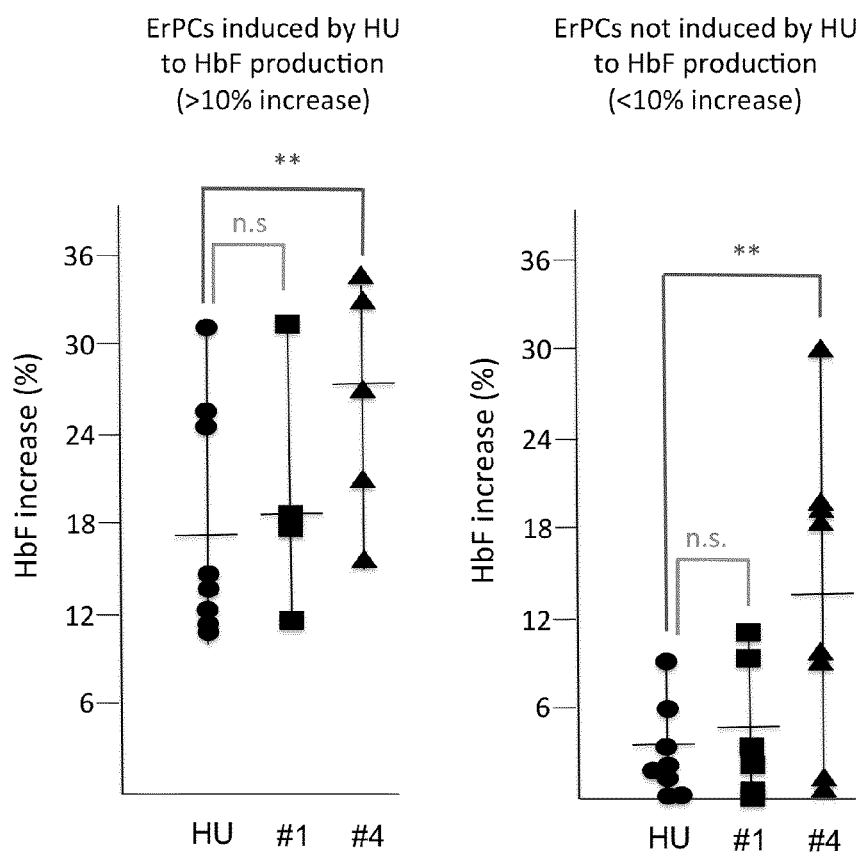
FIG. 4: HbF increase after treatment with isoxazoles of ErPCs able to be induced (left) or not (right) with HU.

The studies performed using all the isoxazoles 1-8 in ErPCs from β-thalassemia patients demonstrate that these derivatives are more efficient than HU (FIG. 4, left). Moreover, the most interesting activity is the capability of some isoxazoles in inducing HbF in erythroid precursors cells resistant to HU (FIG. 4, right). After considering the results shown in FIG. 4, we can conclude that the effects are partly heterogeneous within the studied population of ErPCs. This is an expected result, because it is known that every patient can respond differently to the HbF inducers.

Figure 5:
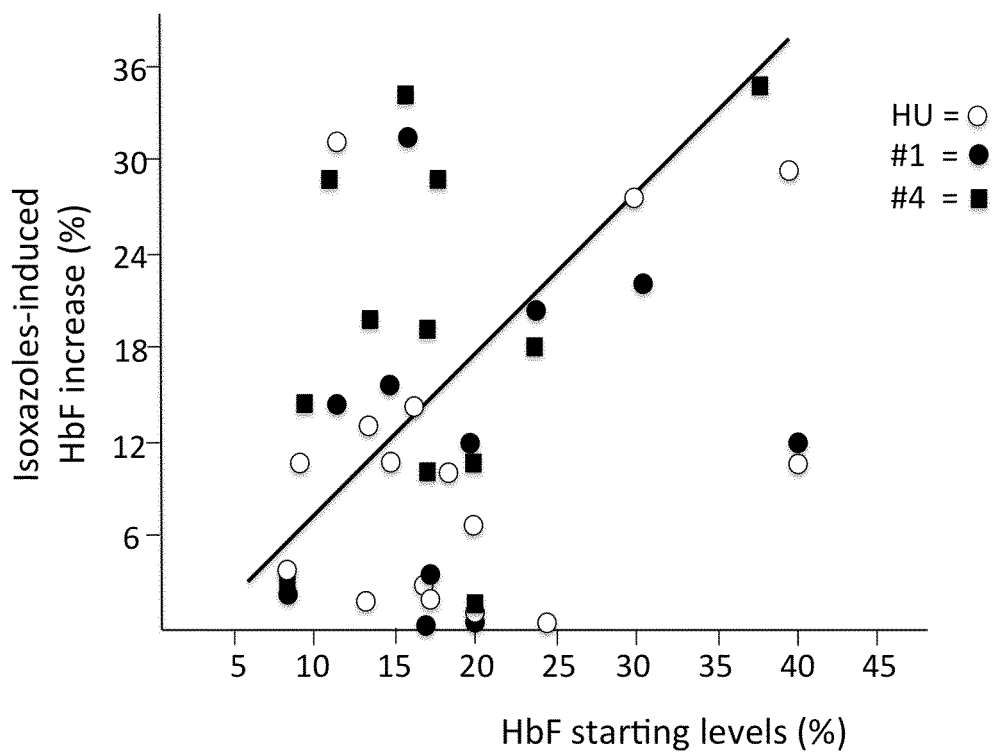
FIG. 5: Relationship between isoxazoles-mediated HbF and starting HbF levels in treated ErPCs.

Data presented in FIG. 5 show an association between the response to the isoxazoles (and HU) and the endogenous HbF starting levels, indicating a strategy to find patients showing high probability in correctly responding to the treatment with isoxazoles.

Representative data shown in FIG. 5 (compounds 1 and 4) were reproducibly obtained for all the analyzed isoxazoles.

For the required therapeutic use, the compounds of the invention will be administered orally or parenterally at doses that will be determined after dose-response studies and after pharmaceutical dynamics and toxicological characterization of the compounds.

The effective doses will typically be between 0.01 and 100 mg/kg.

The invention claimed is:

1. A method to induce fetal hemoglobin for therapeutic treatment of thalassemia and sickle cell disease in patients in need thereof with compounds of formula I

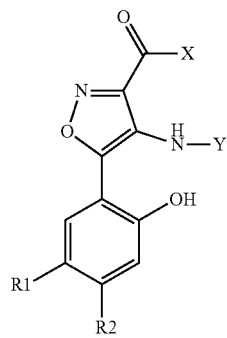

wherein R1 is C1-C3 alkyl or chlorine, fluorine, bromine;
R2 is hydroxy or methyl;
X is a C1-C4 alkylamino group or C1-C4 fluoroalkylamino group;
Y is a C2-C4 acyl group, a benzoyl group, optionally substituted with one or more methoxy, heteroaryl moieties, or a group with the following formula:

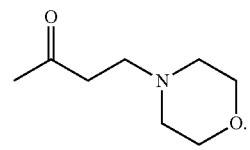

2. The method of claim 1 wherein R1 is chlorine or isopropyl.

3. The method of claim 1 wherein X is ethylamino or 2,2,2-trifluoroethylamino.

4. The method of claim 1 wherein Y is acetyl, tert-butylcarbonyl, para-methoxybenzoyl, 3,4-dimethoxy-benzoyl, 3-methyl-tienyl, 5-acetyl-isoxazolyl.

5. The method of claim 1, wherein said compounds are selected from the group consisting of 1
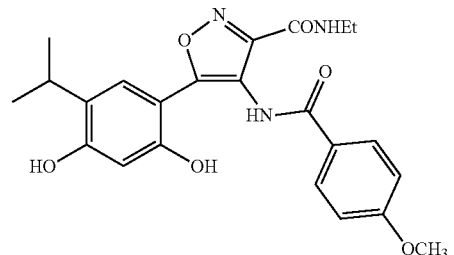
2
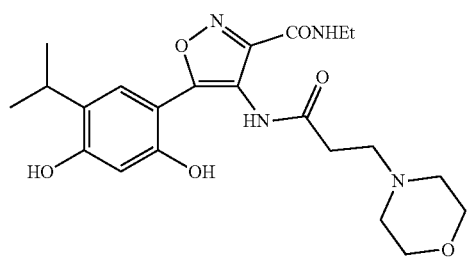
3
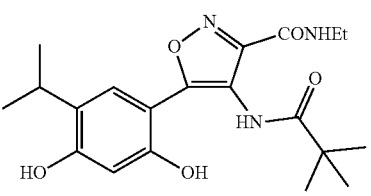
4
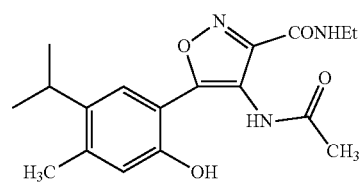
-continued
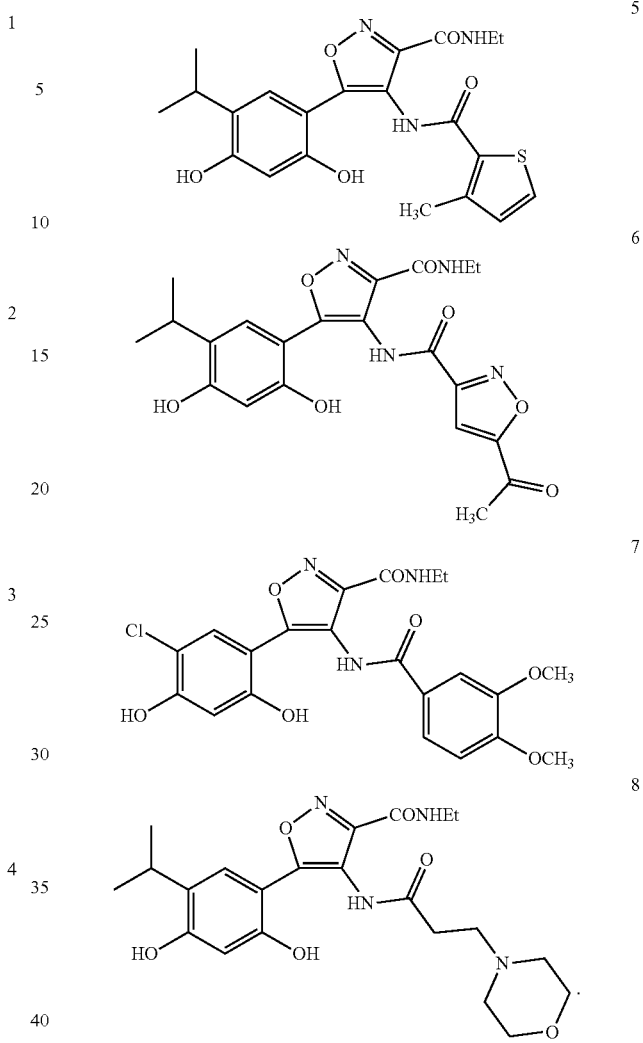
* * * * *